United States Patent [19]
Mehlberg et al.

[11] Patent Number: 5,750,818
[45] Date of Patent: May 12, 1998

[54] ALKYLATION PROCESS

[75] Inventors: Robert L. Mehlberg, Wheaton; James B. Young, Crest Hill, both of Ill.

[73] Assignee: Amoco Corporation, Chicago, Ill.

[21] Appl. No.: 667,841

[22] Filed: Jun. 20, 1996

[51] Int. Cl.$^6$ .............................. C07C 2/56; C07C 2/64; C07C 2/66
[52] U.S. Cl. ................. 585/709; 585/730; 585/731; 585/446; 585/458; 585/462
[58] Field of Search ..................... 585/709, 730, 585/731, 446, 458, 462

Primary Examiner—Glenn Caldarola
Assistant Examiner—In Suk Bullock
Attorney, Agent, or Firm—James R. Henes; Robert A. Yesukevich; Frank J. Sroka

[57] ABSTRACT

A process for cooling unreacted hydrocarbon substrate that is recycled to an alkylation reactor and for minimizing the concentration of lower boiling hydrocarbons in such recycle.

11 Claims, 2 Drawing Sheets 5,750,818

ALKYLATION PROCESS

BACKGROUND OF THE INVENTION

1. Field of the Invention

The present invention relates to a process for the liquid phase alkylation of a hydrocarbon substrate with an olefinic alkylating agent in the presence of an acid alkylation catalyst, and more particularly concerns the recycle and cooling of unreacted hydrocarbon substrate in an aforesaid alkylation process.

2. Discussion of the Prior Art

The olefinic alkylating agents typically employed in the liquid-phase alkylation of a hydrocarbon substrate in the presence of an alkylation catalyst may also be polymerized by contact with the alkylation catalyst. Such competing polymerization reactions occur more readily than do the desired alkylation reaction between the olefinic alkylating agent and the hydrocarbon substrate. In addition, other undesirable side or secondary reactions involving the alkylating agent and/or an alkylation product may also occur under the alkylation conditions employed.

A procedure to inhibit and minimize the occurrence of concurrent polymerization reactions and any other undesirable side or secondary reactions is to effect the catalytic alkylation reaction under conditions that are designed to avoid intimate contact of the olefinic alkylating agent and the alkylation products with the conventional sulfuric acid or hydrofluoric acid catalyst material in the comparative absence of the hydrocarbon substrate. To accomplish this, it has been customary to provide a substantial excess of the hydrocarbon substrate over both the alkylating agent and the alkylation products in the reaction mixture in the reaction zone.

Thus, it has always been necessary to recycle unreacted hydrocarbon substrate to the alkylation reactor. In order to maximize the efficiency of recycle, it is highly desirable to maximize the concentration of the hydrocarbon substrate and to minimize the concentration in the recycle to the alkylation reactor of hydrocarbons that are lower and higher boiling than the unreacted hydrocarbon substrate and that are introduced with the fresh feed.

One aspect of minimizing the concentration of the aforesaid lower and higher boiling materials in the recycle is to improve the efficiency of the removal of such hydrocarbons from the recycle. Typically, isobutane is employed as the hydrocarbon substrate, and butenes and propylene are employed as the alkylating agent. Typically, n-butane and propane are generally present in the isobutane and propylene feeds. Consequently, typically depropanizer and debutanizer towers are employed to remove a portion of propane and n-butane from the unreacted isobutane before it is recycled to the alkylation reactor. Such towers are generally large and expensive. It is therefore highly desirable to improve the efficiency of removing aforesaid lower and higher boiling hydrocarbons such as propane and n-butane from the hydrocarbon substrate such as isobutane without reducing the quantity of the unreacted hydrocarbon substrate that is recycled to the alkylation reactor. Desirably, the improved efficiency of their removal would permit a reduction in the load on the removal means such as the depropanizer and debutanizer towers or would permit an effective increase in the capacity of the alkylation reactor.

Furthermore, the aforesaid liquid-phase alkylation is highly exothermic. In order to maintain the reaction temperature sufficiently low to enhance the occurrence of the desired alkylation reaction and the production of high octane alkylation products over the competing concurrent polymerization reactions and other side or secondary reactions, it has been conventional to cool the recycle and to use the cooled recycle as a refrigerant in the reaction mixture for the conventional sulfuric acid or hydrofluoric acid catalyzed alkylation processes. It is therefore also highly desirable to improve the efficiency of cooling the recycle.

The aforesaid problems of minimizing contact of the alkylating agent and alkylation products with the alkylation catalyst and of removal of exothermal heat from the alkylation reaction zone and maximizing the removal of higher and lower boiling hydrocarbons from the recycled hydrocarbon substrate occur in conventional hydrofluoric acid- or sulfuric acid-catalyzed alkylation reactions and in alkylation systems involving either a vapor phase within the alkylation reactor or no vapor phase within the alkylation reactor.

Furthermore, such problems are greatly exacerbated in an alkylation reaction system in which the alkylation catalyst is adsorbed on a confined volume of particulate contact material within a fixed bed within a reactor and in which this confined volume constitutes the reaction zone and moves from one end to the other end of the reactor and in which there is no vapor phase and no possibility of evaporative cooling within the reactor. Hommeltoft and Topsoe, U.S. Pat. Nos. 5,220,095 and 5,245,100 and Hommeltoft, U.S. Pat. Nos. 5,396,017 and 5,396,018, disclose one such alkylation system for the liquid phase alkylation of an isoparaffin with an olefinic alkylating agent, which comprises passing a process stream of the isoparaffin and alkylating agent under alkylation conditions through a fixed bed alkylation reactor of particulate polar contact material in the presence of a fluorinated sulfonic acid catalyst. The fluorinated sulfonic acid catalyst is adsorbed on a confined area of the polar contact material, which area constitutes the reaction zone. When the process stream is passed in one flow direction through the reactor, the reaction zone in the form of the catalyst adsorbed on the contact material migrates on the contact material in the direction of the flow of the process stream. Thus, during the alkylation reaction, the acid catalyst and consequently the reaction zone moves to a new position in the fixed bed located nearer the outlet end of the alkylation reactor, as a result of interaction with the process stream flowing through and reacting in the reaction zone. The migration speed of the acid catalyst on the contact material in the fixed bed in the reactor is much lower than the migration speed of the hydrocarbons in the process and product streams resulting in a very long elution time for the acid catalyst relative to the elution time for the hydrocarbons in the process and product streams.

OBJECTS OF THE INVENTION

It is therefore a general object of the present invention to provide an improved aforesaid alkylation method that affords the aforesaid desirable features and overcomes the aforesaid problems.

More particularly, it is an object of the present invention to provide an improved aforesaid method that maximizes the recycle to the alkylation reactor of unreacted hydrocarbon substrate.

It is a related object of the present invention to provide an improved aforesaid method that minimizes the concentration in the unreacted hydrocarbon substrate that is recycled to the alkylation reactor of aforesaid hydrocarbons having lower boiling points than the unreacted hydrocarbon substrate.

It is a further object of the present invention to produce an improved aforesaid method that reduces the load on the aforesaid tower for removing the aforesaid lower boiling hydrocarbon from the unreacted hydrocarbon substrate that is recycled to the alkylation reactor.

It is another object of the present invention to provide an improved aforesaid method that improves the efficiency of the recycle of unreacted hydrocarbon substrate as a refrigerant in the alkylation reactor.

Other objects and advantages of the present invention will become apparent upon reading the following detailed description and appended claims.

SUMMARY OF THE INVENTION

These objects are achieved by the improvement of the present invention in a process for the liquid phase alkylation in an alkylation reactor of a hydrocarbon substrate with an olefinic alkylating agent in the presence of an acid alkylation catalyst and at least one hydrocarbon having a lower boiling point than the hydrocarbon substrate and with a substantial stoichiometric excess of the hydrocarbon substrate over the alkylating agent, to form a liquid product mixture comprising alkylation product, aforesaid at least one lower boiling hydrocarbon and unreacted hydrocarbon substrate. The improvement comprises: (a) generating from at least a portion of the liquid product mixture a vapor phase comprising unreacted hydrocarbon substrate and aforesaid lower boiling hydrocarbon; (b) compressing and at least partially condensing the aforesaid vapor phase to form a relatively cooler liquid condensate, wherein if partial condensation takes place, there is produced a liquid condensate which is depleted in the aforesaid lower boiling hydrocarbon and a vapor phase which is enriched in the aforesaid lower boiling hydrocarbon; (c) if total condensation takes place in (b), and optionally if partial condensation takes place in step (b), flashing the liquid condensate from step (b) to form a vapor phase that is enriched in the aforesaid lower boiling hydrocarbon and a further cooled liquid phase that is depleted in the aforesaid lower boiling hydrocarbon; (d) recycling to the alkylation reactor the liquid phase formed from partial condensation in step (b) or from flashing in step (c) or both; and (e) separating the lower boiling hydrocarbon from unreacted hydrocarbon substrate (i) in at least a portion of the vapor phase formed from flashing in step (c) and from partial condensation in step (b) or both, optionally after such vapor phase is compressed or after partial condensation of such vapor phase and removal of the resulting liquid phase, or (ii) in at least a portion of the liquid phase formed by total condensation of such vapor phase.

DETAILED DESCRIPTION OF THE PREFERRED EMBODIMENTS

Figure 1:
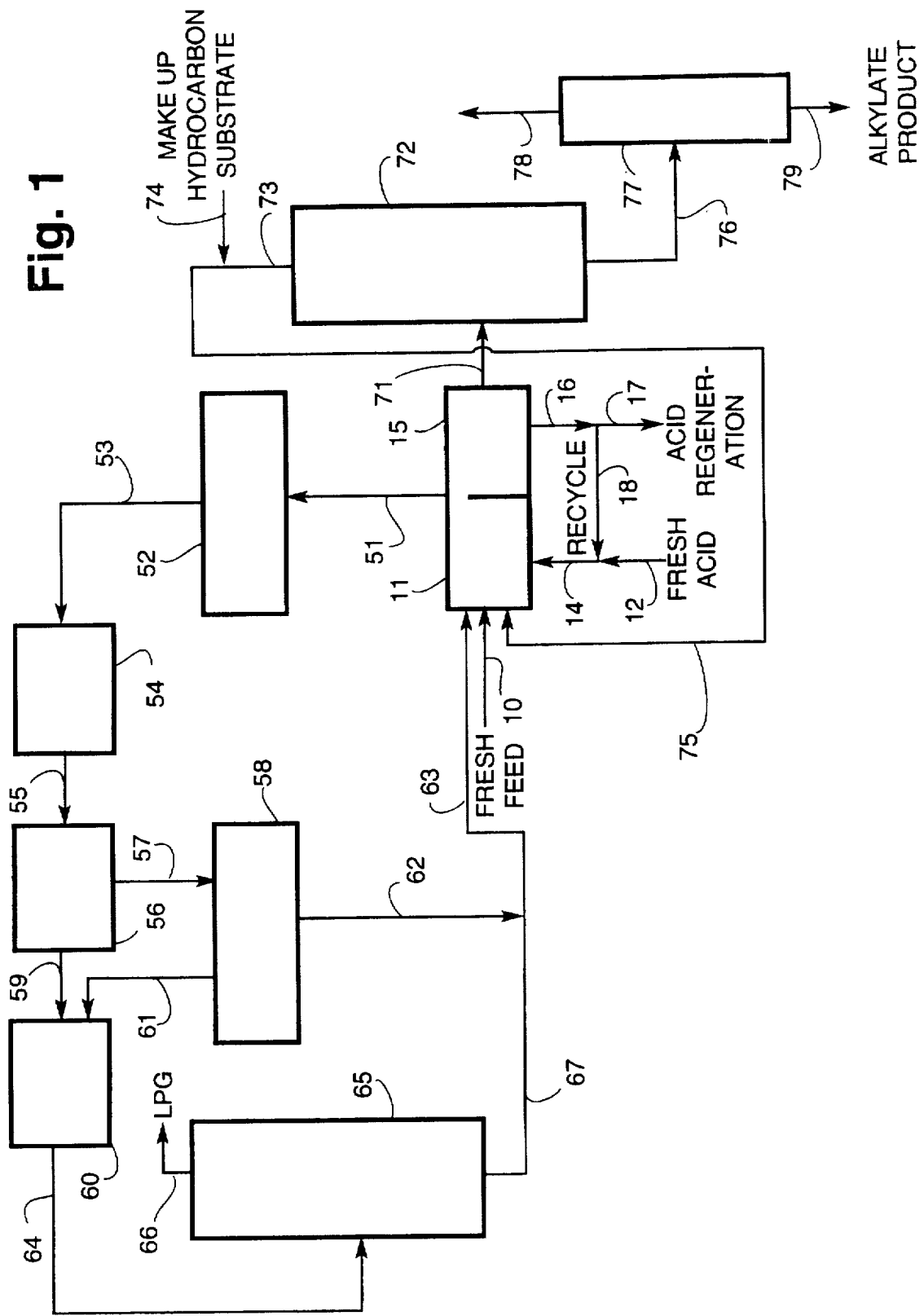
FIG. 1 is a schematic illustration showing a preferred embodiment of the present invention in which a vapor phase is generated within, and withdrawn from, the alkylation reactor and is thereafter partially condensed. The resulting liquid condensate is flashed, and the vapor phases produced from both the partial condensation and the flashing steps are compressed and fed to a tower for separation of the unreacted hydrocarbon substrate from the lower boiling hydrocarbon.

Suitable hydrocarbon substrates for use in the method of this invention include straight and/or branched chain $C_2$ to $C_{10}$ paraffins such as butane, hexane and the like, preferably $C_4$ to $C_6$ isoparaffins such as isobutane, isopentane and isohexane. Volatile aromatic compounds can also be employed as the hydrocarbon substrate in the method of this invention. Suitable volatile aromatic compounds comprise at least one of benzene, toluene and thiophene and preferably comprise both benzene and toluene. The source of the aforesaid suitable hydrocarbon substrates is not limited to any particular refinery stream or gasoline blending stock, and the exact composition of the source refinery stream or blending stock will depend on its source.

Suitable olefinic alkylation agents include $C_2$ to $C_{12}$ terminal and internal monoolefins such as ethylene, propylene, isobutylene, butene-1, butene-2, trimethylethylene, the isomeric pentenes and similar higher monoolefinic hydrocarbons of either a straight chain or a branched chain structure. Preferably, the $C_2$ to $C_6$ monoolefins are used, although the highly-branched $C_7$ to $C_{12}$ monoolefins may also be used. Cycloolefins may also be used. The reaction mixtures may also contain small amounts of diolefins. Although it is desirable from an economic standpoint to use the normally gaseous olefins as reactants, normally liquid olefins may also be used. Thus, the method of the present invention contemplates the use of reactable dimers and trimers and the like of the above-mentioned olefins, such as, for example, the diisobutylene and triisobutylene dimers and trimers, the codimer of normal butylene and isobutylene, of butadiene and isobutylene, and the like. Mixtures of two or more of the olefins above described can also be used as the alkylating agent.

The alkylation catalyst employed in the method of the present invention can be hydrofluoric acid or sulfuric acid or, in the embodiment employing an alkylation reaction system of the type disclosed in aforesaid U.S. Pat. Nos. 5,220,095; 5,245,100; 5,396,017 and 5,396,018, a halogenated sulfuric or halogenated sulfonic acid. Thus, suitable acid catalysts for use in the method of the present invention include fluorinated sulfonic acids such as fluorinated alkane sulfonic acids, in particular, $C_1$ to $C_4$ perfluorinated alkanesulfonic acids. The halogenated sulfonic acid catalyst typically employed is fluorosulfonic acid, trifluoromethanesulfonic acid or trifluoroethanesulfonic acid, and preferably is trifluoromethane-sulfonic acid.

Also suitable for use as the alkylation catalyst in the method of this invention is the class of organosulfonic acids and acid derivatives whose compositions and preparations are described in King et al., U.S. Pat. No. 5,414,187, and were originally described in PCT application WO 90/07480, which was published on Jul. 12, 1990. Such acids have at least one covalent carbonfluorine bond and at least one covalent carbon-phosphorus bond provided by a phosphono radical to increase the acidity of the organosulfonic acid and a Lewis acid complexed with at least a portion of the sulfonic acid groups. In addition, as disclosed in Parker et al., U.S. Pat. No. 3,887,635, the halosulfuric acid or halosulfonic acid alkylation catalyst or both can be used in admixture with one or more moderators as the alkylation catalyst system.

Suitable contact materials for use in the method of the present invention in the embodiment employing an alkylation reaction system of the type disclosed in aforesaid U.S. Pat. Nos. 5,220,095; 5,245,100; 5,396,017 and 5,396,018 include any porous solid that is able to form an adduct with the acid alkylation catalyst and does not react or disintegrate under alkylation conditions. Thus, suitable materials include any of the non-basic materials with polar surface groups and with sufficient adsorption capacity for the acid catalyst relative to that for the hydrocarbons in the reaction and product streams to provide high adsorption rates during passage of the acid catalyst-containing product stream through the contact material. Preferably the support material comprises a solid material with a Hammett acidity $H_o>-8$ calculated on the material in protonated form. Thus, preferred materials are silica, alumina, zirconia, titania, niobium oxide, tin oxides or mixtures thereof. Other suitable materials include polymer resins with pyridine groups, amine groups, other basic groups, or porous forms of carbon including forms of activated carbon. Of these, preferred materials are protonated forms of polyvinyl pyridine crosslinked with divinyl benzene and/or polystyrene amines.

In the method of the present invention, the catalytic alkylation process is carried out in the alkylation reactor at a temperature in the range of from about $-300°$ C., preferably from about $-15°$ C., more preferably from about $0°$ C., to about $100°$ C., preferably to about $50°$ C., more preferably to about $15°$ C. Higher temperatures tend to produce larger amounts of polymeric products and a reduced octane alkylate.

In the method of the present invention, the catalytic alkylation process is carried out in the alkylation reactor at a pressure in the range of from about 1 to about 100 atmospheres, depending on the composition of the process stream and the actual reaction temperature. Where the reaction is carried out at temperatures above about $-10°$ C., it is necessary that the reaction be conducted under super-atmospheric pressure, if both the reactants and catalyst are to be maintained substantially in the liquid state. Typically, the alkylation reaction is conducted at pressures varying from about 1 to 20 atmospheres. Although it is preferred to run the reaction neat, solvents or diluents may be employed if desired.

For the present purposes, the fresh feed to the alkylation reactor in the method of the present invention is the fresh alkylating agent and hydrocarbon substrate introduced into that reactor. Thus, the amount of hydrocarbon substrate that is recycled to the reactor and that is employed essentially as a refrigerant or diluent within the reactor for the fresh feed is not included in the calculation of the amount of fresh feed. The weight ratio, conventionally referred to as the external weight ratio in the alkylation art of the hydrocarbon substrate-to-alkylating agent in the fresh feed is in the range of from about 2, preferably from about 4, and more preferably from about 7, to about 100, preferably to about 20, and more preferably to about 12.

For the present purposes, the total feed to the alkylation reactor employed in the method of the present invention is the combination of the aforesaid fresh feed, and the total amount of hydrocarbon substrate and alkylating agent, if any, recycled to the reactor. Thus, any hydrocarbon substrate that is recycled to the reactor and employed essentially as a refrigerant or diluent within the reactor is included in the calculation of the amount of total feed. The weight ratio, conventionally referred to as the internal weight ratio in the alkylation art, of fresh hydrocarbon substrate to alkylating agent in the reactor is in the range of from about 4, preferably from about 10, and more preferably from about 20, to about 1000, preferably to about 100, and more preferably to about 30.

The method of the present invention comprises the following stages: (a) generating from at least a portion of the liquid product mixture a vapor phase comprising unreacted hydrocarbon substrate and aforesaid lower boiling hydrocarbon; (b) compressing and at least partially condensing the aforesaid vapor phase to form a relatively cooler liquid condensate, wherein if partial condensation takes place, there is produced a liquid condensate which is depleted in the aforesaid lower boiling hydrocarbon and a vapor phase which is enriched in the aforesaid lower boiling hydrocarbon; (c) if total condensation takes place in (b), and optionally if partial condensation takes place in step (b), flashing the liquid condensate from step (b) to form a vapor phase that is enriched in the aforesaid lower boiling hydrocarbon and a further cooled liquid phase that is depleted in the aforesaid lower boiling hydrocarbon; (d) recycling to the alkylation reactor the liquid phase formed from partial condensation in step (b) or from flashing in step (c) or both; and (e) separating the lower boiling hydrocarbon from unreacted hydrocarbon substrate (i) in at least a portion of the vapor phase formed from flashing in step (c) and from partial condensation in step (b) or both, optionally after such vapor phase is compressed or after compression and partial condensation of such vapor phase and removal of the resulting liquid phase, or (ii) in at least a portion of the liquid phase formed by total condensation of such vapor phase.

Thus, in the method of the present invention, alkylation conditions of temperature and pressure are employed in the alkylation reactor either (a) such that the vapor phase of step (a) is generated within the alkylation reactor from the liquid product mixture and is withdrawn from the alkylation reactor or (b) such as to prevent vaporization in the alkylation reactor and the pressure on the liquid reactor effluent is subsequently reduced to permit vaporization and the generation of the vapor phase of step (a) from the reactor effluent. Thereafter the vapor phase produced in step (a) is either partially or totally condensed in step (b). If the vapor phase formed in step (a) is totally condensed in step (b), the resulting cooled liquid condensate is flashed in step (c) to form (i) a vapor phase which is enriched in the aforesaid lower boiling hydrocarbon which is then processed in step (e), and (ii) a cooled liquid phase which is recycled to the alkylation reactor in step (d). If the vapor phase formed in step (a) is partially condensed, the resulting vapor phase is enriched in the aforesaid lower boiling hydrocarbon and is then processed in step (e), and the resulting liquid condensate is either recycled to the alkylation reactor in step (d) or flashed in step (c) to form a vapor phase that is enriched in the aforesaid lower boiling hydrocarbon and is then processed in step (e) and the resulting liquid phase is recycled to the alkylation reactor in step (d).

In step (e), the lower boiling hydrocarbon is separated from the unreacted hydrocarbon substrate in the vapor phase formed in step (b) or (c) or both either (i) without compression of such vapor phase, or (ii) after compression of such vapor phase, or (iii) after compression and partial condensation of such vapor phase and removal of the resulting liquid condensate. In the alternative, the vapor phase formed in step (b) or (c) or both can be totally condensed and the lower boiling hydrocarbon is separated from unreacted hydrocarbon substrate in at least a portion of the resulting liquid condensate.

Figure 2:
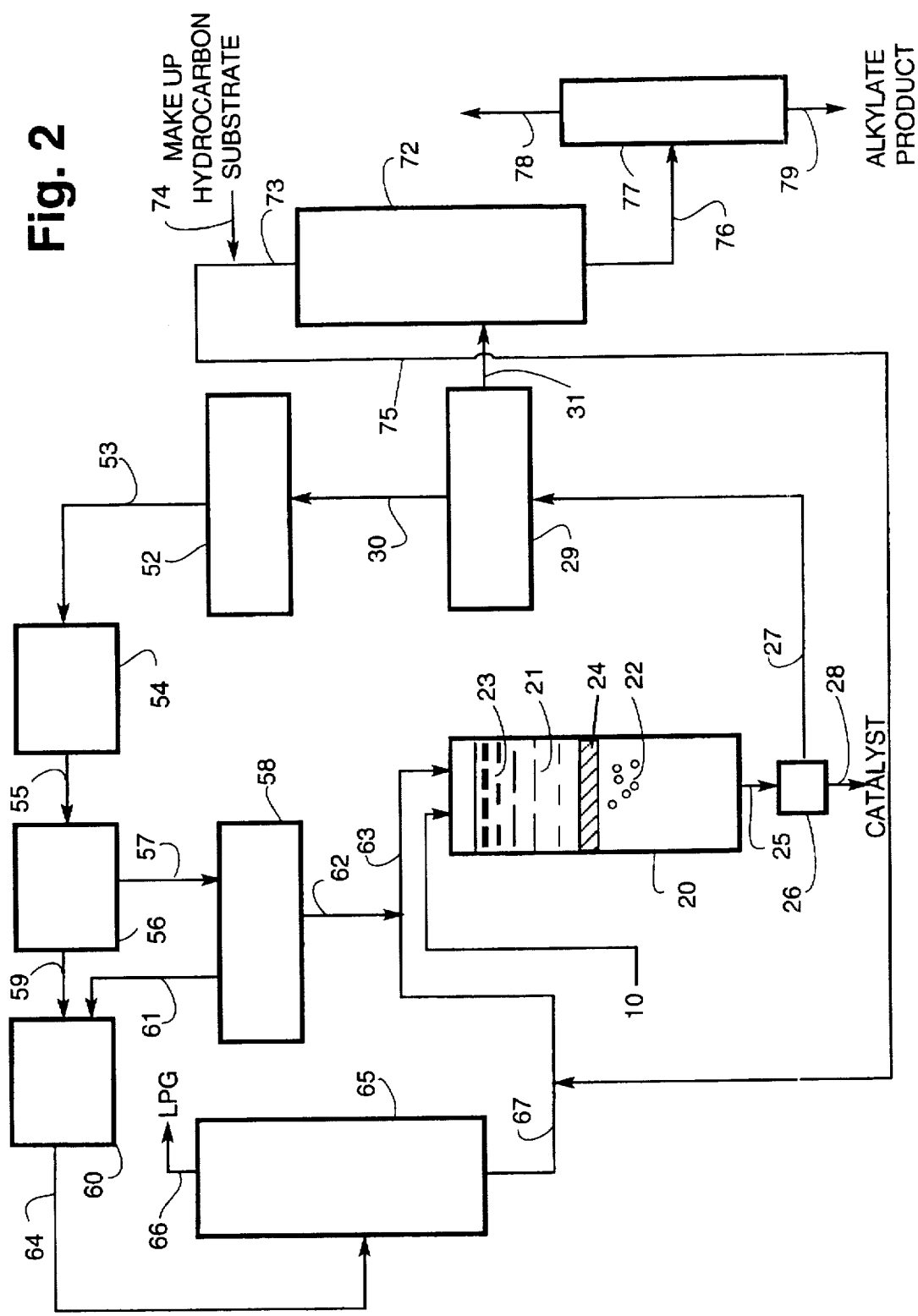
FIG. 2 is a schematic illustration showing another preferred embodiment of the present invention which differs from the embodiment of FIG. 1 in that a vapor phase is not generated within the alkylation reaction but instead a liquid phase is withdrawn from the alkylation reactor and is thereafter flashed to generate a vapor phase which is processed as in FIG. 1.

Several preferred embodiments of the method of this invention are illustrated in FIGS. 1 and 2. It must be pointed out that FIGS. 1 and 2 are schematic illustrations and therefore various features such as pumps and valves, which are conventional parts of a process plant, are not shown in FIGS. 1 and 2. Various alternatives and additional process steps are also omitted for the sake of simplicity.

Turning now to FIG. 1, a fresh charge of hydrocarbon substrate and alkylating agent are introduced through the line 10 into the alkylation reactor 11. Fresh alkylation acid catalyst in the line 12 and recycle acid catalyst in the line 13 are combined in line 14 and introduced into the reactor 11. The liquid alkylation product mixture and acid catalyst pass from the alkylation reactor 11 to the settler 15, where an alkylation catalyst phase separates from the alkylation product mixture phase. The alkylation catalyst is withdrawn from the settler 15 through the line 16 and a portion thereof is recycled through the lines 13 and 14 back to the alkylation reactor 11 and the remainder thereof is withdrawn through the line 17 for regeneration.

The alkylation reaction is performed in the alkylation reactor 11 under conditions of temperature and pressure such that a vapor phase comprising the aforesaid lower boiling hydrocarbon and unreacted hydrocarbon substrate is formed. The vapor phase is withdrawn from the reactor 11 and settler 15 through the line 51 and introduced into the knock out drum 52 where any entrained liquid is removed from the gas stream and returned (not shown) to the settler 15. The remaining vapor is withdrawn in the line 53 from the drum 52 and passed to the compressor 54 where the vapor stream is pressurized. The compressed vapor stream is then passed in the line 55 to a partial condenser 56 where the compressed vapor stream is partially condensed to form a liquid enriched in the hydrocarbon substrate and depleted in the lower boiling hydrocarbon, which passes through the line 57 to the flash drum 58, and a vapor phase enriched in the lower boiling hydrocarbon, which passes in the line 59 to an appropriate stage of the compressor 60. The liquid enriched in the hydrocarbon substrate is flashed in the flash drum 58 to form another vapor phase enriched in the lower boiling hydrocarbon, which is withdrawn in the line 61 and passed to an appropriate stage of the compressor 60, and a liquid phase further enriched in the hydrocarbon substrate which is recycled through the lines 62 and 63 to the alkylation reactor 11.

The compressed vapor enriched in the lower boiling hydrocarbon is then passed in the line 64 from the condenser 60 to a tower 65 to separate the lower boiling hydrocarbon from the hydrocarbon substrate and to condense each. The liquefied lower boiling hydrocarbon is withdrawn from the tower 65 in the line 66 for recovery, and the liquefied hydrocarbon substrate is withdrawn from the tower 65 and recycled to the alkylation reactor 11 in the lines 67 and 63. Typically, the hydrocarbon substrate is isobutane and the lower boiling hydrocarbon is propane. In that case, the tower 65 can be any conventional depropanizer.

The liquid phase containing the alkylation product mixture is withdrawn from the settler 15 in the line 71 and introduced into the tower 72 where unreacted hydrocarbon substrate is separated from higher boiling materials such as the alkylation product. Hydrocarbon substrate is withdrawn from the tower 72 in line 73, combined with makeup hydrocarbon substrate from line 74 and the combination is recycled to the reactor 11 through the line 75. When the hydrocarbon substrate is isobutane, the tower 72 is a conventional deisobutanizer or isobutane stripper, and n-butane is typically present as well and is separated with the alkylation product and other higher boiling materials as a bottoms fraction, which are then withdrawn from the tower 72 through the line 76 and introduced into the tower 77, where the alkylation product is separated from the relatively lighter components, such as n-butane, of this stream. The alkylation product is removed for recovery through the line 79, and the other components are withdrawn from the tower 77 through the line 78. When n-butane is present, the tower 77 is a debutanizer.

Another preferred embodiment of the method of this invention is shown in FIG. 2. Elements in the embodiment of FIG. 2 that correspond to elements in the embodiment of FIG. 1 are numbered the same as the corresponding elements in the embodiment of FIG. 1. The only differences between the embodiments of FIGS. 1 and 2 are that instead of the alkylation reactor of FIG. 1 in which a vapor phase exists, the embodiment of FIG. 2 employs an alkylation reaction system in which the alkylation catalyst is adsorbed on a confined volume of particulate contact material within a fixed bed within a reactor and in which this confined volume constitutes the reaction zone and moves from one end to the other end of the reactor and in which there is no vapor phase and no possibility of evaporative cooling within the reactor. Hommeltoft and Topsoe, U.S. Pat. Nos. 5,220,095 and 5,245,100 and Hommeltoft, U.S. Pat. Nos. 5,396,017 and 5,396,018, disclose such an alkylation system for the liquid phase alkylation of an isoparaffin with an olefinic alkylating agent, which comprises passing a process stream of the isoparaffin and alkylating agent under alkylation conditions through a fixed bed alkylation reactor of particulate polar contact material in the presence of a fluorinated sulfonic acid catalyst. The fluorinated sulfonic acid is adsorbed on a confined area of the polar contact material, which area constitutes the reaction zone. When the process stream is passed in one flow direction through the reactor, the reaction zone in the form of the catalyst adsorbed on the contact material migrates on the contact material in the direction of the flow of the process stream. Thus, during the alkylation reaction, the acid catalyst and consequently the reaction zone moves to a new position in the fixed bed located nearer the outlet end of the alkylation reactor, as a result of interaction with the process stream flowing through and reacting in the reaction zone. The migration speed of the acid catalyst on the contact material in the fixed bed in the reactor is much lower than the migration speed of the hydrocarbons in the process and product stream resulting in a very long elution time for the acid catalyst relative to the elution time for the hydrocarbons in the process and product streams.

In one embodiment disclosed in aforesaid U.S. Pat. No. 5,220,095, when the reaction zone approaches the outlet end of the alkylation reactor, the flow direction of the process stream through the fixed bed in the alkylation reactor is reversed to thereby cause the reaction zone to reverse its direction of movement in the fixed bed and to move nearer the opposite end of the alkylation reactor by interaction with the process stream as described above. It is thus possible to reuse the acid catalyst without recovering the acid.

In another embodiment disclosed in aforesaid U.S. Pat. No. 5,245,100, having reached the outlet end of a first reactor, the acid catalyst elutes from the fixed bed in the first reactor and is transferred together with the product stream to the inlet end of a second reactor which also contains a fixed bed of a polar contact material. The acid catalyst is then adsorbed within a confined area of the contact material in the fixed bed within the second reactor and processed therein as in the first reactor. When the acid catalyst elutes from the fixed bed in the second reactor and passes out of the outlet of the second reactor, it is recycled to the inlet end of the first reactor.

As shown in FIG. 2, a fresh supply of a suitable hydrocarbon substrate and a suitable alkylating agent are introduced through line 10 into the reactor 20 which contains a fixed bed 21 of a suitable contact material 22. A suitable halogenated sulfuric acid or halogenated sulfonic acid alkylation catalyst is previously deposited on the surface of a confined volume 23 of particulate contact material at the top of bed 21. The acid catalyst is adsorbed strongly on the contact material that constitutes the reaction zone 24, and only traces exit from the reactor 20 in the product stream through the line 25. The reaction zone 24 is shown at the middle of the bed 21 of contact material 22 in the reactor 20. The band width of adsorbed acid within the reaction zone 24 is determined by the number of theoretical plates and the capacity of the contact material 22 used. Within the reaction zone 24, the process stream is converted at alkylation conditions to a product stream containing alkylation products and unreacted hydrocarbon substrate and, if any, unreacted alkylating agent. Because of the high rate of the alkylation reaction under typical alkylation conditions and the high ratio of hydrocarbon substrate to alkylating agent in the process stream, generally there is essentially no unreacted alkylating agent in the product stream leaving the reactor 20 through the line 25.

During the alkylation reaction, the acid catalyst and, consequently, the reaction zone 24 continually move downward to new positions within the bed 21 located nearer the outlet end of the reactor 20 by interaction of the acid catalyst with the process stream and product stream flowing downward through the bed 21. The migration speed of the acid catalyst (and hence the reaction zone 24) in the bed 21 in the reactor 20 is lower than the migration speed of the hydrocarbons in the process and product streams through the bed 21, resulting in a very long elution time for the acid catalyst compared to the elution time for the hydrocarbons, during which time the activity of the acid catalyst is substantially retained, and the acid is still catalytically active when the catalyst (and the reaction zone 24) reaches the outlet of the reactor 20.

When the reaction zone 24 reaches or nears the bottom of the reactor 20, another batch of acid catalyst is introduced into the confined volume 23 of the particulate contact material 22 at the top of the bed 21 of contact material 22 within the reactor 20, from which it also continually moves downward, as described hereinabove. When the acid catalyst exits from the reactor 20 through the line 25 in the product stream, the product stream passes from the reactor 20 in the line 25 to the separator 26 where acid catalyst is separated from the product stream. Any conventional convenient separation device or system can be employed as separator 26. One suitable system is a liquid-liquid decanter. The resulting substantially catalyst-free product stream then passes in line 27 and the separated acid catalyst passes through the line 28 for recovery and reintroduction into the alkylation reactor, optionally after regeneration. The product stream in line 27 is then introduced into a flash drum 29 where it is flashed to form a vapor phase comprising primarily unreacted hydrocarbon substrate, for example isobutane, and aforesaid lower boiling hydrocarbon, for example propane, and a liquid phase comprising alkylation products, the remainder of the unreacted hydrocarbon substrate and other relatively higher boiling hydrocarbons. The vapor phase is withdrawn from the flash drum 29 through the line 30 to the knock out drum 52, and the liquid phase is withdrawn through the line 31 to the tower 72.

The benefits of the method of this invention can be illustrated by reference to a conventional or prior art system for removing propane from an isobutane recycle stream from an alkylation reactor. The particular conventional system differs from the embodiment of the method of this invention shown in FIG. 1 in that in the conventional system, condenser 56 is a total condenser from which the resulting liquid condensate is split such that 83 weight percent thereof is recycled directly to the alkylation reactor and 17 weight percent thereof is led directly to the depropanizer 65. Thus, in the conventional system, flash drum 58 and compressor 60 are not employed.

In two embodiments (Embodiments A and B) of the method of this invention, modifications of the embodiment illustrated in FIG. 1 were employed. In Embodiment A, condenser 56 was a partial condenser with about 15% of its throughput passing in line 59 as a vapor to the compressor 60 and about 85% being recycled to the alkylation reactor. No flashing occurs in flash drum 58, and no vapor passes in line 61 from the flash drum 58 to the compressor 60. The vapor in line 59 is compressed in compressor 60 and fed as a vapor directly into the depropanizer 65.

In Embodiment B, condenser 56 is a total condenser such that no vapor passes in line 59 and the liquid condensate is flashed in flash drum 58 such that about 40% passes as a vapor through the line 61 from flash drum 58 to the compressor 60. The remaining 60% passes as a liquid to the alkylation reactor. A total condenser (not shown) located in line 64 condenses all of the vapor from the compressor 60. The resulting condensate is split such that 55% of the condensate is fed directly to the depropanizer 65 and the remaining 45% of the condensate is fed to the flash drum 58.

The results of the use of the conventional system above and of Embodiments A and B are presented in Table 1 hereinbelow.

TABLE 1

| | Conventional System | Embodiment A | Embodiment B |
|---|---|---|---|
| Propane in Refrigerant Recycle to Reactor, vol. % | 27 | 14 | 14 |
| Alkylation Catalyst, Makeup, pounds per gallon of alkylate | 0.46 | 0.41 | 0.41 |
| Alkylation Product Octane (R + M)/2 | 91.03 | 91.18 | 91.20 |
| Alkylation Product Yield, vol. % based on olefin | 172 | 174 | 174 |
| Total Horsepower per barrel of alkylate | 6.6 | 7.1 | 6.8 |

The results in Table 1 illustrate that by enriching the feed to the depropanizer in propane, the method of the present invention affords a substantial reduction in the propane content in the isobutane recycle stream to the alkylation reactor and thus an increase in the ratio of isobutane-to-olefin in the reactor, and a greater yield of a higher octane number alkylation product and a substantial reduction in the amount of alkylation catalyst makeup required. This enrichment effectively doubles the depropanizer capacity for only a 5–9% increase in total horsepower.

From the above description, it is apparent that the objects of the present invention have been achieved. While only certain embodiments and various modifications have been described, numerous alternative embodiments and various modifications will be apparent from the above description to those skilled in the art. These alternatives and embodiments are considered equivalents and within the spirit and scope of the present invention.

Having described the invention, what is claimed is:

1. In a process for the liquid phase alkylation in an alkylation reactor of a hydrocarbon substrate with an olefinic alkylating agent in the presence of an acid alkylation catalyst and a hydrocarbon having a lower boiling point than the hydrocarbon substrate and with a substantial stoichiometric excess of the hydrocarbon substrate over the alkylating agent, to form a liquid product mixture comprising alkylation product, aforesaid at least one lower boiling hydrocarbon and unreacted hydrocarbon substrate, the improvement comprising:

(a) generating from at least a portion of the liquid product mixture a vapor phase comprising unreacted hydrocarbon substrate and lower boiling hydrocarbon;

(b) compressing and at least partially condensing the aforesaid vapor phase to form a relatively cooler liquid condensate, wherein when partial condensation takes place, there is produced a liquid condensate which is depleted in the lower boiling hydrocarbon and a vapor phase which is enriched in the lower boiling hydrocarbon;

(c) when total condensation takes place in step (b), and optionally if partial condensation takes place in step (b), flashing the liquid condensate from step (b) to form a vapor phase which is enriched in the lower boiling hydrocarbon and a further cooled liquid phase which is depleted in the lower boiling hydrocarbon which is recycled to the reactor;

(d) recycling to the alkylation reactor the liquid phase formed from partial condensation in step (b) or from flashing in step (c) or both; and (e) separating the lower boiling hydrocarbon from unreacted hydrocarbon substrate (i) in at least a portion of the vapor phase formed from flashing in step (c) or from partial condensation in step (b) or both, optionally after such vapor phase is compressed or after compression and partial condensation of such vapor phase and removal of the resulting liquid phase, or (ii) in at least a portion of the liquid phase formed by total condensation of such vapor phase.

2. The process of claim 1 wherein alkylation conditions of temperature and pressure are employed such that the vapor phase of step (a) is generated within the alkylation reactor from the liquid product mixture and is withdrawn from the alkylation reactor.

3. The process of claim 1 wherein alkylation conditions of temperature and pressure are employed such as to prevent vaporization in the alkylation reactor and the pressure on the liquid reactor effluent is subsequently reduced to permit vaporization and the generation of the vapor phase of step (a) from the reactor effluent.

4. The process of claim 1 wherein the vapor phase from step(a) is totally condensed in step (b).

5. The process of claim 1 wherein the vapor phase from step (a) is partially condensed in step (b).

6. The process of claim 5 wherein the resulting liquid condensate from step (b) is flashed in step (c).

7. The process of claim 5 wherein the resulting liquid condensate from step (b) is recycled to the alkylation reactor in step (d).

8. The process of claim 1 wherein in step (e) the lower boiling hydrocarbon is separated from the unreacted hydrocarbon substrate in the vapor phase formed in step (b) or (c) or both without compression of such vapor phase.

9. The process of claim 1 wherein in step (e) the lower boiling hydrocarbon is separated from unreacted hydrocarbon substrate in the vapor phase formed in step (b) or (c) or both after compression of such vapor phase.

10. The process of claim 1 wherein in step (e) the lower boiling hydrocarbon is separated from unreacted hydrocarbon substrate in the vapor phase formed in step (b) or (c) or both after such vapor phase is compressed and partially condensed and after the resulting liquid condensate has been removed.

11. The process of claim 1 wherein in step (e) the lower boiling hydrocarbon is separated from unreacted hydrocarbon substrate in at least a portion of the liquid phase formed by total condensation of the vapor phase formed in step (b) or (c) or both.

* * * * *

UNITED STATES PATENT AND TRADEMARK OFFICE
CERTIFICATE OF CORRECTION

PATENT NO.: 5,750,818
DATED: May 12, 1998
INVENTOR(S): Robert L. Mehlberg, James B. Young It is certified that error appears in the above-identified patent and that said Letters Patent is hereby corrected as shown below:

Patent reads:

| Col. | Line | |
|---|---|---|
| 4 | 55 | reads "covalent carbonfluorine bond" should read --covalent carbon-fluorine bond-- |
| 5 | 20 | reads "from about -300°C.," should read --from about -30°C.,-- |

Signed and Sealed this

Ninth Day of February, 1999

Attest:

Attesting Officer

Acting Commissioner of Patents and Trademarks